United States Patent [19]

Kitchin

[11] Patent Number: 4,988,340
[45] Date of Patent: Jan. 29, 1991

[54] TUBULAR DRAINAGE DEVICE

[76] Inventor: Christopher Kitchin, 5098 Rootstown Rd., Ravenna, Ohio 44266

[21] Appl. No.: 343,916

[22] Filed: Apr. 26, 1989

[51] Int. Cl.$^5$ .............................................. A61M 27/00
[52] U.S. Cl. ...................................................... 604/280
[58] Field of Search ..................... 433/81, 224; 604/29, 604/264, 266, 268, 280, 285, 332, 355

[56] References Cited

U.S. PATENT DOCUMENTS

| | | | |
|---|---|---|---|
| 2,436,623 | 2/1948 | Van Zile | 433/81 |
| 3,704,520 | 12/1972 | Weissman | 433/224 |
| 4,015,607 | 4/1977 | Wright, III | 604/264 |
| 4,687,471 | 8/1987 | Twardowski et al. | 604/175 |
| 4,772,261 | 9/1988 | Von Hoff et al. | 604/51 |
| 4,795,446 | 1/1989 | Fecht | 604/264 |
| 4,820,306 | 4/1989 | Gorman et al. | 623/16 |
| 4,828,491 | 5/1989 | Gray | 433/136 |
| 4,936,834 | 6/1990 | Beck et al. | 604/264 |

Primary Examiner—John D. Yasko
Assistant Examiner—Adam J. Cermak
Attorney, Agent, or Firm—Oldham & Oldham Co.

[57] ABSTRACT

Drainage device for dental or medical or veterinary purposes. The preferred device, for dental purposes, comprises an elongated tube and a flange near one end (the drainage end) thereof. The flange has suture holes to facilitate suturing to the patient's gum. Representative dimensions for dental purposes are: overall length, 0.25–2 inch; outside diameter of tube, 0.04–0.2 inch; inside diameter of tube, 0.02–0.1 inch; tube wall thickness, 0.01–0.05 inch; diameter of flange, not more than 0.5 inch. The device is made of a biocompatible resilient elastomer. To use, the dentist cuts a hole through the patient's gum to the abscess site in the usual manner, inserts the insertion end of the tube (the end remote from the flange) so that it is at the abscess site and sutures the flange to the patient's gum.

8 Claims, 2 Drawing Sheets

TUBULAR DRAINAGE DEVICE

TECHNICAL FIELD

This invention relates to drainage devices for dental, and use. In particular, this invention relates to a dental abscess drainage device which is capable of being sutured to gum of a patient and draining an abscess.

BACKGROUND ART

Conventional practice for draining a periodontal abscess (i.e., an abscess in the gum or bone adjacent to a tooth) is to make an incision through the gum to the abscess site, insert a drainage tube, commonly either a dam drain or a Penrose drain, and allow the abscess to drain for several days (e.g. three or four days), until the pus has been drained. Only after the abscess has been drained can the dentist treat the site to rid it of infection.

The dam drain is not manufactured as a drain, but rather in the form of square sheets of a pharmaceutically acceptable grade of rubber or latex (e.g. "Natsyn" rubber) which may be cut to desired size and rolled into a tube at the dentist's office and inserted into the patient's mouth at the incision site by the dentist. Actually, the primary purpose of the dental dam is simply to keep the incision open until the abscess has drained, rather than to form a device for fashioning into a drainage tube.

The other widely used device is a Penrose drain. The Penrose drain is a collapsible tube, made of a pharmaceutically acceptable x-ray opaque rubber in various sizes. It is generally flat as packaged and shipped. It may be folded. The Penrose drain is manufactured primarily for medical and veterinary use, rather than dental use, although it is available in small sizes suitable for dental use. The Penrose drain may be (and frequently is) cut to desired size.

One difficulty with both the dental dam and the Penrose drain is that neither is prone to stay in place for the entire time (about three or four days) required for dental drainage. One reason for this is that the dam and the Penrose drain can be sutured to the gum only with great difficulty. In addition, the drain fashioned from a dental dam may not hold its shape over the entire time required.

Although both the dental dam and the Penrose drain leave something to be desired, they nevertheless represent the best drainage aids available and are the most widely used drainage aids. What is needed is a drainage aid which will stay in place for the entire length of time required for drainage and will effectively serve as a conduit to drain pus away from the abscess.

DISCLOSURE OF THE INVENTION

The present invention provides a drainage device for dental or use, which may be sutured to a body tissue of the patient and which will stay in place long enough for drainage of an abscess or other unwanted fluid.

The drainage device of this invention comprises an elongated resilient tubular member, open at both ends, and resilient attaching means extending outwardly from the exterior of the tubular member. The attaching means is suturable to body tissue. The preferred attaching means is a thin flat resilient flange o ring at right angles to the longitudinal axis of the tubular member. The flange may be provided with a plurality of evenly spaced suture holes arranged in a circle.

According to a preferred embodiment of the invention, the drainage device is of a size and configuration for dental use. The flange is near one end of the tubular member in this embodiment. The flange may be sutured to a patient's gum.

BEST MODE FOR CARRYING OUT THE INVENTION

Figure 1:
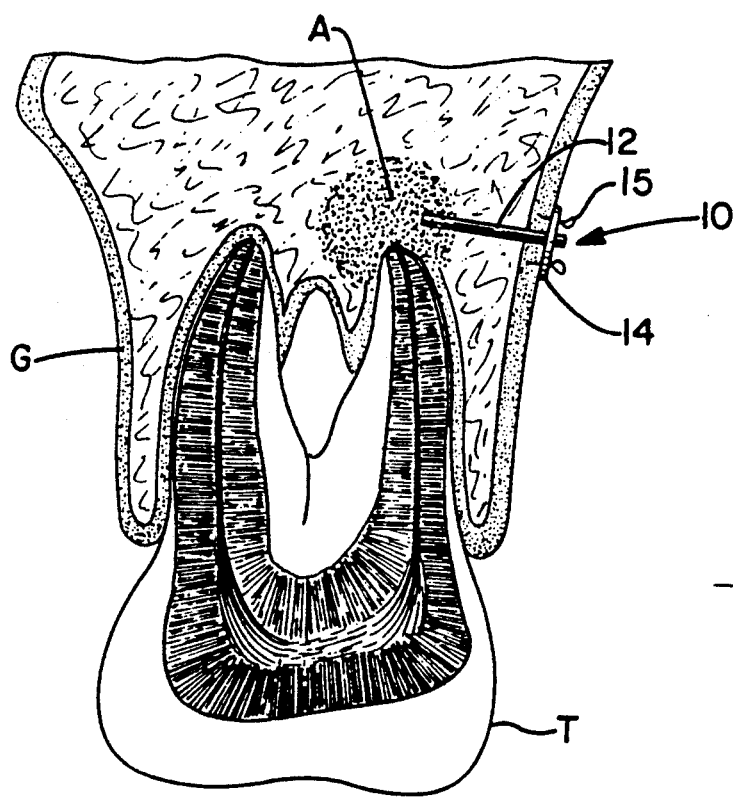
FIG. 1 is a schematic elevational view of an abscess site, including a tooth, the adjacent gum, and an abscess, showing the drainage device of this invention sutured in place for drainage of the abscess.

Shown in FIG. 1 is a dental drainage device 10 of this invention, sutured in place for draining pus from abscess A. This abscess as shown is next to the root of a patient's tooth T. Gum G surrounds the root but not the crown of tooth T. (Only one tooth and the gum adjacent thereto are shown.) Device 10 includes an elongated tubular member (or tube) 12 and a flange 14 near one end (the drainage or outlet end) of tube 12. Device 10 is sutured to the gum G by means of sutures 15, which may pass through holes to be shown in FIG. 2 in flange 14. The drainage device 10 is positioned so that one end of the tube (the inlet or insertion end, which is the end remote from flange 14) extends into the abscess A while the other end of the tube (the drainage end) is in the frontal portion of the patient's mouth, in front of the teeth. Tube 12 is open at both ends so that pus can drain from abscess A.

Drainage device 10 is made of a sterilizable biocompatible resilient elastomer, e.g., "Natsyn" rubber. ("Natsyn" is a registered trademark of Goodyear Tire and Rubber Co., Akron, Ohio, and is understood to denote a cis-1,4-polyisoprene rubber). In addition to being biocompatible and resilient, "Natsyn" rubber is also capable of holding sutures without tearing. Since device 10 is elastomeric, it is flexible and resilient, so that it can bend as necessary for insertion into a patient's gum, and has memory, so that it will return to its original shape when no stress is applied.

The device 10 and its use are illustrated with particular reference to a human patient, although it will be apparent that the device may be used for drainage of dental abscesses in other vertebrate animals and in particular other mammals.

Figure 2:
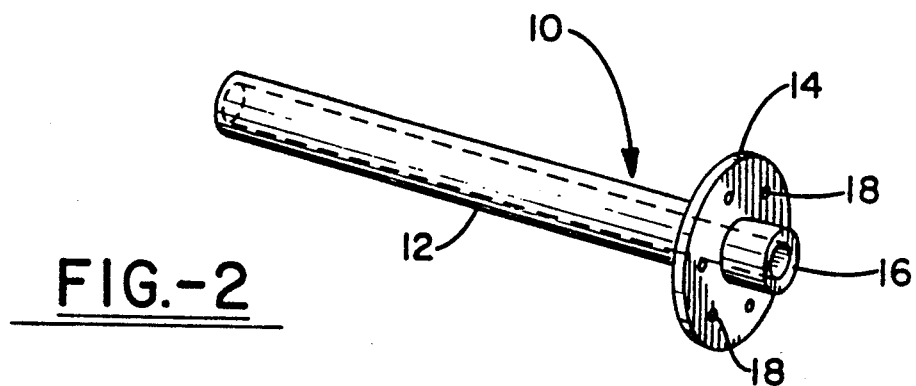
FIG. 2 is a perspective view of the drainage device, according to a preferred embodiment of this invention.
Figure 3:
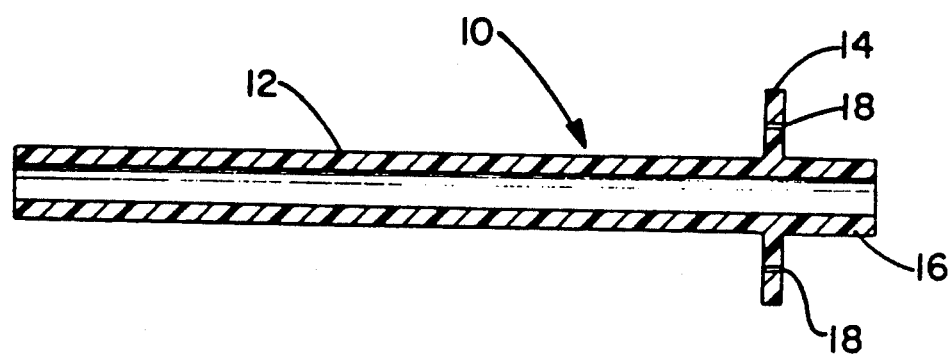
FIG. 3 is a longitudinal sectional view of the drainage device of FIG. 2.

The preferred drainage device 10 of this invention is shown in detail in FIGS. 2 and 3. This preferred embodiment is intended primarily for dental use. Referring now to FIGS. 2 and 3, drainage device 10 according to this embodiment, includes an elongated tubular member or tube 12, open at both ends, and a thin flat flange (or collar or ring) 14, which is joined to tube 12 near (but not precisely at) one end (the drainage end) thereof. Flange 14 extends radially outwardly from the exterior of tube 12 and is disposed at right angles to the axis of tube 12. Flange 14 is provided for attachment (via suturing, for example) of drainage device 10 to gum G (or other body part in the case of other embodiments to be described subsequently).

The length of tube 12 may be from about 5 to about 20 times the outside diameter of tube 12. A preferred length/outside diameter ratio is about 10 to 15. The diameter of flange 14 (measured at the outer edge) is typically from about 2 to about 4 times the outside diameter of tube 12. These limits are not critical. The diameter of the flange may be less, as long as the annular width (which is one-half the difference between the diameter of flange 14 and the outside diameter of tube 12) is sufficient to receive and retain sutures 15.

The wall thickness of tube 12, and the thickness of flange 14, are sufficient so that the device 10 is resilient rather than collapsible, but not so great that tube 12 and flange 14 are stiff.

Tube 12 has a short nose portion 16 between the flange 14 and the adjacent outlet end of tube 12. This nose portion 16 directs pus away from the flange 14 and thereby makes drainage more efficient. The axial length of nose portion 16 can be quite short, typically from about 0.2 to 1 times the outside diameter of tube 12.

Flange 14 may be (and preferably is) provided with a plurality of equally spaced suture holes 18, through which sutures 15 (shown in FIG. 1) may pass. The presence of these sutures holes makes suturing of the device 10 to the patient's gum easier, by eliminating flange 14 as a resistance element through which the suture needle must pass.

The overall length of drainage device 10 for dental purposes is typically (and preferably) from about 0.25 inch (0.63 cm) to about 2 inches (5 cm). The inside diameter of tube 12 is typically about 0.02 inch to about 0.1 inch (0.5 to 2.5 mm), and the outside diameter of tube 12 is typically about 0.04 inch to about 0.2 inch (1 to 5 mm) and is normally about twice the inside diameter. The wall thickness of tube 12, which is one-half the difference between the inside diameter and the outside diameter, is typically from about 0.01 inch to about 0.05 inch (0.025 to 0.125 cm, or 0.25 to 1.25 mm). The diameter of flange 14 normally does not exceed 0.5 inch (1.25 cm). The flange diameter is normally at least 0.04 inch (1 mm) greater than the outside diameter of tube 12, in order to permit effective suturing to the gum G. Typical dimensions herein stated are also preferred. A drainage device 10 having these dimensions and made of "Natsyn" rubber or other suitable biocompatible elastomer will be both flexible and resilient.

Device 10 may be made by conventional injection molding techniques. When injection molding is used, flange 14 is formed integrally with tube 12.

Representative dimensions of a dental drainage device 10 are given in Table I below. Dimensions are in inches, with corresponding dimensions in millimeters given in parentheses.

TABLE I

| Item | Inches (mm) |
| --- | --- |
| Tube 12 | |
| overall length | 1 9/16 (39.7) |
| outside diameter | ⅛ (3.2) |
| inside diameter | 1/16 (1.6) |
| wall thickness | 1/32 (0.8) |
| length of nose 16 | 1/32 (0.8) |
| Disk 14 | |
| maximum diameter | ⅜ (9.6) |
| thickness | 1/32 (0.8) |

Dimensions given in Table I above are representative of a preferred embodiment and are not by way of limitation.

The length of tube 12 in the device 10 as manufactured is preferably the maximum length that is likely to be needed in a dental drainage device. Tube 12 may be easily cut to desired lengths, depending on the needs of the individual patient.

Various modifications can be made without departing from this invention. For example, while flange 14 has been shown as a flat disk, disposed at right angles to the axis of tube 12, flange 14 may be disposed at some angle, say 60°, to the axis of tube 12. (Usually the angle between the plane of flange 14 and the axis of tube 12 is at least 60°). It may be either a frustoconical member or a spherically curved member (one hemisphere or less, usually less). Also, instead of flange 14 as shown, the attaching means may consist of two or more wings, radiating from the axis of tube 12 as the center and usually spaced equiangularly (e.g., 180° when there are two wings).

While tube 12 is normally straight, it may be bent when "at rest" (i.e., when no stress is applied). For example, tube 12 may be bent, usually at or near flange 14, to form an obtuse angle, e.g., about 120° to about 135°, although more broadly anywhere from about 90° to about 180°. Flange 14 may be perpendicular to the nose portion 16 of the bent tube 12. A bent tube may be advantageous in certain situations for insertion into a patient's gum.

Holes may be provided near the insertion end of tube 12 to provide additional entrances for pus.

Figure 4:
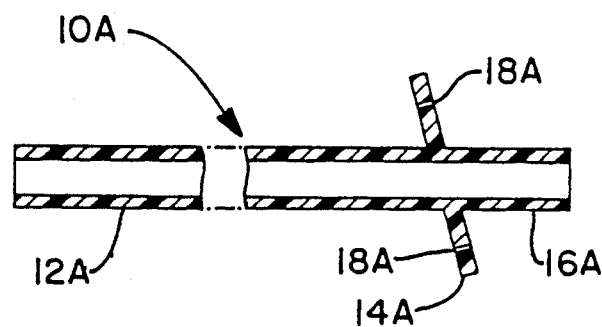
FIG. 4 is a longitudinal view of an alternative form of the drainage device of this invention.

FIG. 4 is a longitudinal sectional view of a dental drainage device according to an alternative embodiment of this invention. Referring now to FIG. 4, 10A shows a dental drainage device according to an alternative embodiment thereof. Device 10A comprises a tube 12A, having a flange 14A disposed at an acute angle (shown here as 60° for purpose of illustration) with respect to the axis of tube 12A. Flange 14A is a flat disc disposed near one end (the draining or outlet end) of tube 12A. Device 10A has a short nose portion 16A between flange 14A and the adjacent end of the tube 12. Flange 14A has a plurality of spaced suture holes 18A. Device 10A of this embodiment is similar to device 10 of the embodiment previously described, except that disc 14A is disposed at an acute angle rather than at a right angle with respect to the axis of the tube 12.

A dental procedure in which the drainage device 10 of this invention is used may be as follows:

(1) The dentist makes an incision (usually vertical) through the gum from the exterior to the abscess A.

(2) The dentist then inserts the drainage device 10, remote end (the end away from flange 14) first, to determine the length required.

(3) The dentist then pulls out the drainage device 10 and cuts it to the needed length.

(4) The dentist then replaces the device 10, remote end first, so that tube 12 extends from the abscess A to the exterior of gum G, with flange 14 on the exterior of the gum.

(5) The dentist then sutures the flange 14 of device 10, to the patient's gum G. Usually two suture ties are sufficient. Sutured device is shown in FIG. 1. Suturing holds the drainage device 10 in place as long as needed for drainage, even if the patient presses the tip of his or her tongue against the device. Suturing also holds the device in place so that the patient can chew and eat normally.

(6) Pus is allowed to drain from the abscess A until drainage is substantially complete. This normally requires about three or four days.

Step 1 above is conventional, as those skilled in the art will recognize. The remaining steps illustrate use of the drainage device 10 of this invention.

The dentist may insert gauze into the abscess site A, surrounding the insertion end of tube 12, if desired to absorb pus. This step may be carried out as step 1A between steps 1 and 2.

The drainage device 10 can also be used to drain unwanted fluids (lymph, for example) from the side of a newly extracted wisdom tooth.

All embodiments of this invention are preferably formed from a pharmaceutically acceptable or biocompatible elastomer (one which is both non-toxic and tolerated by the adjacent tissue) which is also resilient and tear resistant. A preferred material is "Natsyn" rubber, although other pliable (both flexible and resilient) elastomers may be used. Pliability is highly desirable since it is often necessary to bend the tubular portion of the device for proper insertion.

Drainage devices 10 of this invention are intended for a single use. They are preferably sterilized at the factory. They may be packaged individually by known sterile packaging techniques, e.g., by use of blisterwrap to encase each device individually. They may be sterilized according to known techniques either before or after packaging. The latter is preferred since it is then not necessary to assure absolute sterility during packaging.

Figure 5:
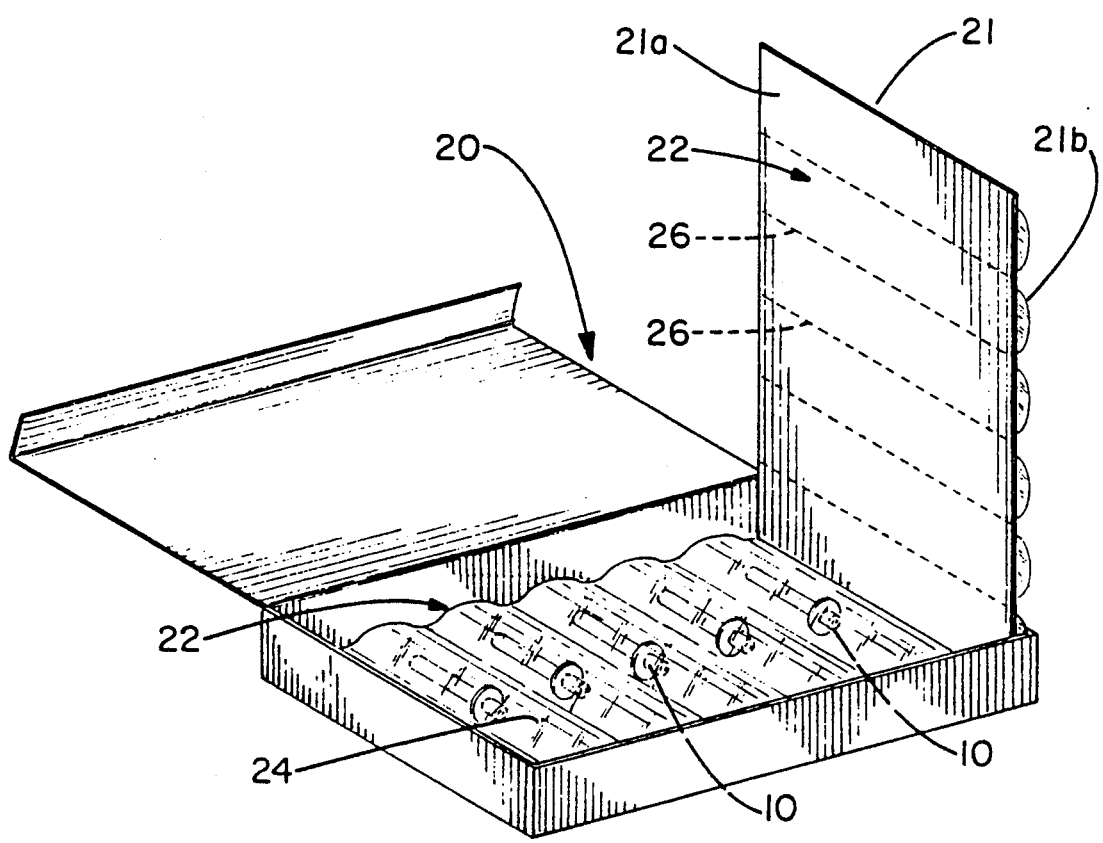

FIG. 5 shows a package 20 of sterile devices 10 according to this invention. Package 20 contains a plurality (2 are shown) of individual blister wrap sheets 21, each of which contains a plurality of individual sterile unit packages of blister packettes 22, each containing one drainage device 10. Blister sheet 21 is a laminate composed of a thin flat flexible plastic base sheet, 21a (preferably transparent) and an undulating thin flexible plastic cover sheet 21b. Undulations occur along only one axis (the longitudinal axis) and so are visible from the side. The undulations include ridges and valleys at regular intervals. The valleys touch the base sheet 21a, and the base sheet 21a and cover sheet 21b are sealed together where they are in touching engagement. The base sheet and cover sheet are also sealed together along the respective side edges. In that manner, base sheet 21a and cover sheet 21b together form a plurality of sealed unit packages or packettes 22. The seals are airtight and provide aseptic enclosures. Conventional sealing techniques, such as heat sealing, may be used. Blister sheet 21 is scored along transversely extending cut lines 26, which are at junctions of base sheet 21a and cover sheet 21b (i.e., at the valleys and cover sheet 21b). These cut lines make it easy for the user to detach individual packettes 22 one at a time from a sheet 21.

The plastic materials forming sheets 21a and 21b must be capable of being sterilized, and must be capable of being torn by hand for the convenience of a user of device 10. At the same time these sheets must be tough enough to resist inadvertent or premature carrying before the user tears off and opens a unit package 22. Suitable materials are known in the package industry.

The user, usually a dentist, tears off a single packette 22 by tearing sheet 21 along a cut line 26, then opens the packette by tearing, removes the device 10, and sutures device 10 to an appropriate body tissue (e.g., a gum G) on the patient as previously described.

The present invention provides a drainage device which is safe, tolerated by body tissue without undesirable effects, easy to install, capable of being sutured, capable of remaining in place once it is installed, and effective to drain unwanted body fluids such as pus from a predetermined location in the body of the patient. The preferred form of this invention, shown in FIGS. 1-3, is particularly useful in draining pus from a dental abscess, and fulfills a long-felt need for a dental drainage device which will stay in place as long as it is needed and which will effectively drain an abscess.

While in accordance with the patent statutes only the best mode and preferred embodiment of the invention has been illustrated and described in detail, it is to be understood that the invention is not limited thereto or thereby, but that the scope of the invention is defined by the appended claims.

What is claimed is:

1. A one piece molded suturable dental drainage device comprising:
    (a) an elongated resilient tubular member open at both ends, and
    (b) a resilient flange for suturing the device to the gum of a patient, said flange being integrally formed with said tube, said flange being located near but not precisely at one end of said tube so that a small portion of said tube extends beyond said flange,
said flange having a plurality of spaced suture holes,
said device being made of cis-1,4-polyisoprene rubber.

2. A drainage device according to claim 1 wherein the ratio of the length to the outside diameter of said tubular member is from about 5 to about 20.

3. A package for dental drainage device, said package comprising a plurality of drainage devices according to claim 1, and means forming a container for said devices.

4. A device according to claim 1 wherein said tube has an overall length of 0.25 to 2 inches, and inside diameter of 0.02 to 0.01 inch, and an outside diameter of 0.04 to 0.2 inch, and wherein the ratio of length to outside diameter is from about 5 to about 20.

5. A one piece molded suturable dental drainage device comprising:
    (a) an elongated resilient cylindrical tube open at both ends and having a longitudinal axis, and
    (b) a resilient flange for suturing the device to the gum of a patient, said flange being integrally formed with said tube, said flange being located near but not precisely at one end of said tube so that a small portion of said tube extends beyond said flange, wherein the length of said small portion of said tube is in the range of about 0.2 to about 1 times the outside diameter of said tube,
said flange having a plurality of spaced suture holes,
said device being made of a biocompatible elastomeric material which is flexible and resilient.

6. A drainage device according to claim 5 wherein said flange is disposed at an acute angle to the axis of said tubular member.

7. A device according to claim 5 wherein said cylindrical tube has an overall length of 0.25 to 2 inches, an inside diameter of 0.02 to 0.1 inch and an outside diameter of 0.04 to 0.2 inch.

8. A device according to claim 5 wherein said flange is circular and is at right angles to the axis of said cylindrical tube.

* * * * *